(12) United States Patent
Link et al.

(10) Patent No.: US 7,311,732 B2
(45) Date of Patent: Dec. 25, 2007

(54) SYSTEM OF INTERVERTEBRAL PROSTHESES

(75) Inventors: Helmut D. Link, Hamburg (DE); Arnold Keller, Kayhude (DE)

(73) Assignee: Link Spine Group, Inc., Branford, CT (US)

( * ) Notice: Subject to any disclaimer, the term of this patent is extended or adjusted under 35 U.S.C. 154(b) by 0 days.

(21) Appl. No.: 10/358,387

(22) Filed: Feb. 5, 2003

(65) Prior Publication Data
US 2004/0073313 A1 Apr. 15, 2004

(30) Foreign Application Priority Data
Oct. 14, 2002 (DE) .................. 102 47 762

(51) Int. Cl.
*A61F 2/44* (2006.01)
(52) U.S. Cl. ................................. 623/17.15
(58) Field of Classification Search .. 623/17.11–17.16, 623/23.57, 23.75, 23.76, 11.11, 16.11, 23.4, 623/23.41; 606/60, 61, 69, 70, 71
See application file for complete search history.

(56) References Cited

U.S. PATENT DOCUMENTS

| | | | |
|---|---|---|---|
| 5,306,308 A | 4/1994 | Gross et al. | |
| 5,314,477 A * | 5/1994 | Marnay | ............ 623/17.15 |
| 5,401,269 A * | 3/1995 | Buttner-Janz et al. | ... 623/17.15 |
| 5,514,180 A | 5/1996 | Heggeness et al. | |
| 6,093,205 A | 7/2000 | McLeod et al. | |
| 6,113,637 A * | 9/2000 | Gill et al. | ............ 623/17.15 |
| 6,368,350 B1 | 4/2002 | Erickson et al. | |
| 6,395,034 B1 | 5/2002 | Suddaby | |
| 6,416,551 B1 * | 7/2002 | Keller | ............ 623/17.15 |
| 6,517,580 B1 * | 2/2003 | Ramadan et al. | ......... 623/17.15 |
| 6,592,624 B1 * | 7/2003 | Fraser et al. | ............ 623/17.16 |
| 6,770,095 B2 * | 8/2004 | Grinberg et al. | ......... 623/17.14 |
| 6,805,714 B2 * | 10/2004 | Sutcliffe | ............ 623/17.11 |

FOREIGN PATENT DOCUMENTS

| | | |
|---|---|---|
| EP | 0 176 728 A1 | 4/1986 |
| EP | 0955021 A1 * | 11/1999 |
| EP | 1 250 898 A1 | 10/2002 |
| WO | WO 9310725 * | 6/1993 |
| WO | WO 00/13619 A1 | 3/2000 |
| WO | WO 02/080818 A1 | 10/2002 |

* cited by examiner

*Primary Examiner*—Anuradha Ramana
(74) *Attorney, Agent, or Firm*—Dickstein, Shapiro, LLP.

(57) ABSTRACT

System of intervertebral prostheses which comprise a prosthesis core (5) and two cover plates (4, 6) which enclose the prosthesis core (5) by way of internal engaging surfaces (7). The system includes corrective cover plates (6) whose vertebral contact surface (12) is lengthened in the AP direction dorsally beyond the extent of standard prostheses (4). In sagittal section, the corrective cover plates are dorsally thickened, in particular wedge-shaped. The inner face (11) of the part (10) constituting the dorsal lengthening is beveled or recessed.

3 Claims, 1 Drawing Sheet

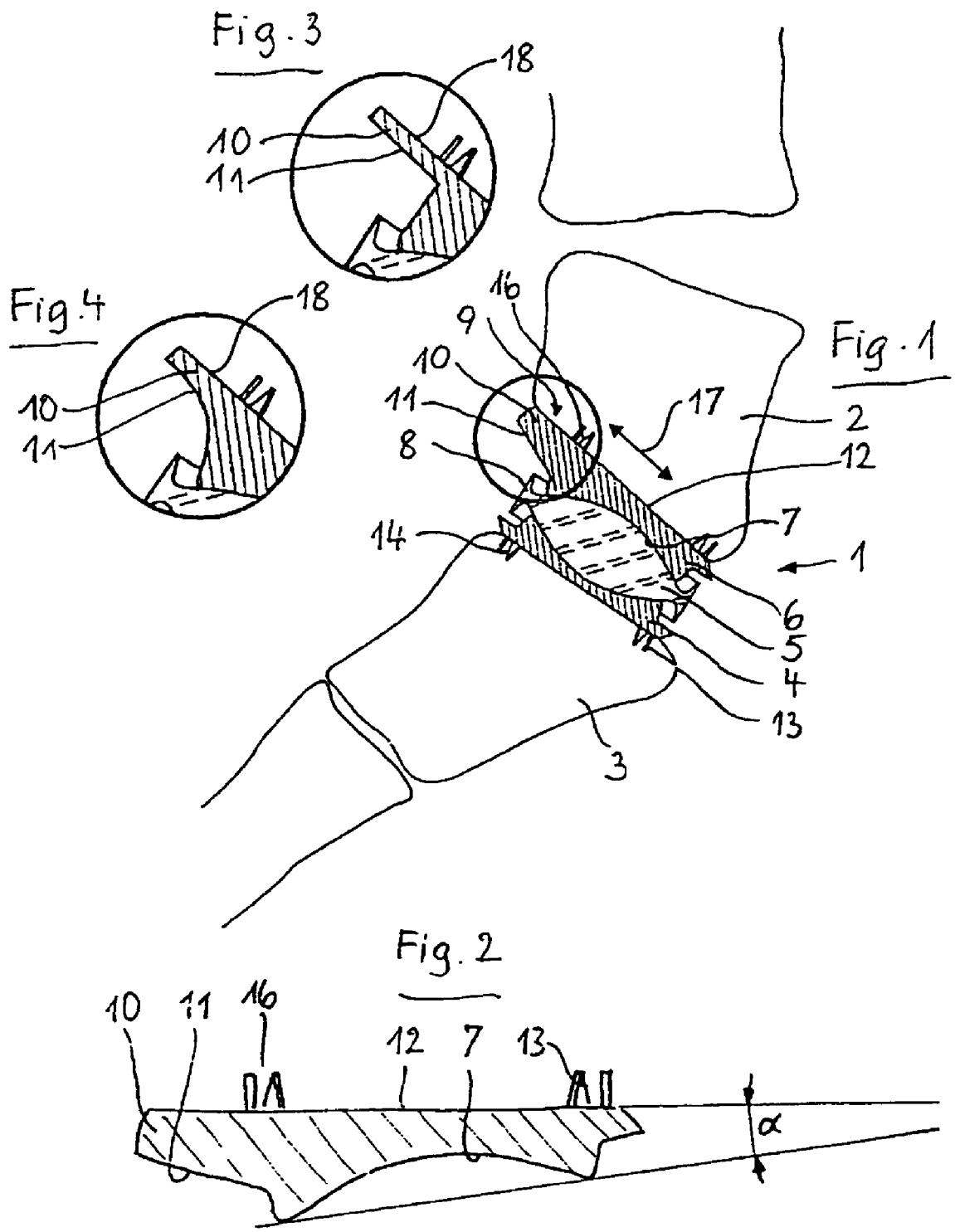

SYSTEM OF INTERVERTEBRAL PROSTHESES

BACKGROUND OF THE INVENTION

A number of cases have been reported in which the caudal, dorsal portion of the fifth lumbar vertebral body has become greatly worn or has collapsed after prosthesis implantation. The risk of collapse arises if the vertebra has been worn away in the dorsal area and the remaining dorsal lip breaks off or too much is removed. This finding, which is part of the inventive achievement, leads to the object of making available an intervertebral prosthesis which in such a case reduces the risk of collapse. This is achieved by using the corrective cover plate specified in claim 1.

The prior art also includes (PCT/EP02/03132=WO 02/080818) a corrective plate whose internal engaging surfaces, compared to normal prostheses, are offset in the AP direction in relation to the contact surface. This affords the possibility of positioning the joint center of a prosthesis elsewhere than is the case in standard prostheses.

SUMMARY OF THE INVENTION

The intervertebral prostheses of the system according to the invention consist of two cover plates and a prosthesis core. On their inner side directed toward one another, the cover plates have engaging surfaces which are designed as sliding articulation surfaces or holding surfaces complementary to the surfaces of the prosthesis core. On their outsides, the cover plates form vertebral contact surfaces which are intended to bear against the associated vertebral bodies and possibly to be secured thereon. The system consists principally of standard prostheses whose vertebral contact surfaces can be kept ready in different sizes and have a predetermined dimension in the antero-posterior direction. The position of the ventral and dorsal edges of the vertebral contact surfaces of the standard prostheses also has a predetermined spatial relationship to the position of the internal engaging surfaces of the cover plates.

The corrective cover plate according to the invention differs from the standard cover plates in that the vertebral contact surface is lengthened in the AP direction dorsally beyond the AP extent of the standard cover plates, and in that it is dorsally thickened in sagittal section. As a result of the thickening, the loss of substance on the vertebral body is wholly or partially compensated. As a result of the lengthening, the vertebral contact surface is extended dorsally and thus reduces the loading of the weakened bone area. The lengthening is made possible by the fact that the bone surface which has been changed compared to the normal state has gained in size at the dorsal end.

The thickening is advantageously wedge-shaped. The wedge shape expediently extends over the entire AP extent of the cover plate. In some cases, however, it can also be sufficient to start the wedge shape at a distance from the ventral edge, for example in the central area of the cover plate.

It is true that cover plates which are wedge-shaped in the sagittal direction for intervertebral prostheses are known (public prior use by the Applicant). In these, the thicker side of the wedge generally lies on the ventral side in order to compensate the lumbar lordosis in which the intervertebral space widens on the ventral side. However, a case has also already been reported (public prior use by the Applicant) in which known wedge-shaped plates of this kind were fitted with the thickened side in the dorsal direction. This results, however, in an incorrect positioning of the joint center and of the force transmission. This is avoided by the dorsal lengthening according to the invention, together with the dorsal wedge-shaped increase in thickness.

The wedge angle of the cover plate is expediently between 5° and 20°.

According to an important feature of the invention, the inner face of the part of the corrective cover plate forming the lengthening can shelve away toward the edge and toward the vertebral contact surface. It is as it were beveled. This bevel can be rectilinear or recessed. The recess can have an arc-shaped or stepped profile. It provides free space for the margin of the slide core or anatomically natural parts which are located in proximity.

It is known to provide the vertebral contact surfaces with teeth which penetrate into the adjoining vertebral body and fix the position of the cover plate in relation to the vertebral body. In the standard prostheses, these teeth are mostly arranged along the ventral edge and dorsal edge. By contrast, in the corrective cover plates according to the invention, the dorsal teeth are expediently provided at a greater distance from the dorsal edge, namely preferably where they are located in relation to the engaging surfaces in the standard cover plates. The reason for this measure is that, in cases where the corrective cover plate is used, the bone substance in proximity to the edge margin of the prosthesis is often weakened as a result of wear, and it is therefore better to arrange the teeth in more solid bone substance lying farther forward.

BRIEF DESCRIPTION OF THE FIGURES

The invention is explained in more detail below with reference to the drawing which depicts an advantageous illustrative embodiment, and in which:

FIG. 1 shows, in sagittal section, an intervertebral prosthesis equipped with a corrective cover plate and in the implanted state, FIG. 2 shows the corrective cover plate on an enlarged scale in sagittal section, and FIGS. 3 and 4 show partial views of alternative configurations according to the circle indicated in FIG. 1.

DETAILED DESCRIPTION OF THE PREFERRED EMBODIMENTS

FIG. 1 illustrates the use of the prosthesis 1 between the fifth lumbar vertebra 2 and the sacrum 3. The prosthesis 1 consists of a lower, standard cover plate 4, a prosthesis core 5, and a corrective cover plate 6. This is a construction in which both cover plates 4, 6 have spherical sliding articulation surfaces 7 acting as engaging surfaces via which they interact with the prosthesis core 5. The latter has a collar 8 which prevents it from escaping from its insertion space if the cover plates 4, 6 were to open unusually wide on either side in the event of flexion movement.

The vertebral body 2 is worn away unusually severely in its dorsal, caudal area 9. As a result, its surface directed toward the prosthesis appears dorsally lengthened. To compensate this, the corrective cover plate is wedge-shaped, with a greater thickness toward the dorsal side. It also has a part 10 which is lengthened dorsally beyond the dorsal limit of the standard plates thereby forming shelf 18. In the embodiment shown in FIGS. 1 and 2, the inside 11 of this lengthened part 10 extends obliquely, so that its inner edge does not protrude too far dorsally and so that the dorsal collar 8 of the prosthesis core has sufficient space during flexion movement. According to the examples in FIGS. 3 and 4, the inner face 11 can also be more distinctly stepped or can form a rounded recess. The important fact is that the dorsal length of the part 10 leads to the formation of a support surface which is longer in the AP direction 17 than in normal circumstances and through which the force transmission is distributed over a greater surface area and the dorsally weakened bone is spared.

FIG. 2 illustrates the measurement of the wedge angle α between the main direction of the engaging surfaces 9 (or their edge) on the one hand and the main direction of the vertebral contact surface 12, on the other. In the case illustrated, the angle is approximately 8°. It can also be slightly greater or slightly smaller. In this case, the main direction of the sliding articulation surfaces 7 is determined on the basis of its peripheral margin. The main direction of the vertebral contact surface 12 coincides with its direction, as it is flat. If it is curved, its middle direction is to be regarded as the main direction.

FIG. 1 shows that in the standard cover plate 4 the teeth 13, 14 are arranged near the ventral edge and the dorsal edge. These are teeth which, because of their sharpness, penetrate into the bone surface when, following insertion of the prosthesis between the spread-open vertebral bodies 2, 3, this spreading is reversed and the tensioning of the ligaments or the load of the bodyweight presses the vertebral contact surfaces 12 of the prosthesis perpendicularly against the associated vertebra.

Unlike the teeth 14 of the standard cover plate, the dorsal teeth 16 of the corrective cover plate are not arranged near the dorsal edge of the vertebral contact surface 12, but arranged approximately where they are also located in the standard cover plate 4 (in relation to the engaging surfaces 7). This is based on the assumption that, at this location, there will be more resistant bone substance than there is near the ventral edge of the cover plate.

The use of the invention is not limited to the prosthesis type illustrated. It can instead also be used if sliding articulation surfaces are provided only on one cover plate, while only retaining members for the prosthesis core 5 are present on the other cover plate. Finally, it can also be used when both cover plates are connected rigidly to the prosthesis core 5 and the movement of the joint is provided for within the prosthesis core 5.

The invention claimed is:

1. An intervertebral prosthesis comprising:
a prosthesis core;
a standard cover plate which encloses the prosthesis core via a first internal engaging surface; and
a corrective cover plate which encloses the prosthesis core via a second internal engaging surface, the second internal engaging surface having an anterior rise and a posterior rise defining a concave second internal engaging surface, the posterior rise being greater than the anterior rise;
wherein the standard cover plate has a first external surface of a first extent between a first dorsal edge and a first ventral edge across an entire sagittal section of the intervertebral prosthesis, the first external surface configured to contact a first vertebral surface and having a predetermined position in relation to the first vertebral surface, and wherein the corrective cover plate has a second external surface of a second extent between a second dorsal edge and a second ventral edge across an entire sagittal section of the intervertebral prosthesis, the second external surface being configured to contact a second vertebral surface, the corrective cover plate having a first ventral thickness at the second ventral edge and a second dorsal thickness in sagittal section at the second dorsal edge;
the second extent of the corrective cover plate being greater than the first extent of the standard cover plate in an anterior-posterior direction dorsally, and
the second dorsal thickness being greater than the first ventral thickness wherein a dorsal thickening of the corrective cover plate is wedge-shaped, said wedge shape starting at the posterior rise and terminating at the second dorsal edge.

2. The intervertebral prosthesis according to claim 1, having a second wedge shape that extends over the entire anterior-posterior extent of the corrective cover plate.

3. The intervertebral prosthesis according to claim 2, wherein the second wedge-shape is defined by a wedge angle (α) in sagittal section between the second internal engaging surface and the second external surface is the wedge angle being between 5° and 20°.

* * * * *